United States Patent
Jacobsen et al.

(10) Patent No.: US 9,232,985 B2
(45) Date of Patent: Jan. 12, 2016

(54) NAVIGATING A SURGICAL INSTRUMENT

(71) Applicant: Medtronic Xomed, Inc., Jacksonville, FL (US)

(72) Inventors: Brad Jacobsen, Erie, CO (US); Ali Mowlai-Ashtiani, Jacksonville, FL (US); Bruce M. Burg, Louisville, CO (US); Ross Smetzer, Valley Springs, CA (US); Steven L. Hartmann, Superior, CO (US); Andrew Bzostek, Boulder, CO (US); Matthew J. Nadeau, Lafayette, CO (US); Matthew W. Koenig, Dacono, CO (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 0 days.

(21) Appl. No.: 13/959,123

(22) Filed: Aug. 5, 2013

(65) Prior Publication Data
US 2013/0317355 A1    Nov. 28, 2013

Related U.S. Application Data

(63) Continuation of application No. 12/400,951, filed on Mar. 10, 2009, now Pat. No. 8,504,139.

(51) Int. Cl.
*A61B 5/055* (2006.01)
*A61B 19/00* (2006.01)
(Continued)

(52) U.S. Cl.
CPC ............ *A61B 19/5244* (2013.01); *A61B 5/062* (2013.01); *A61B 8/0841* (2013.01);
(Continued)

(58) Field of Classification Search
CPC .... A61B 19/5244; A61B 19/54; A61B 17/16; A61B 17/32; A61B 5/062; A61B 2019/5251; A61B 2019/5272; A61B 2019/5483
See application file for complete search history.

(56) References Cited

U.S. PATENT DOCUMENTS

| 4,317,078 A | 2/1982 | Weed et al. |
| 4,788,987 A | 12/1988 | Nickel |

(Continued)

FOREIGN PATENT DOCUMENTS

| AU | 2011245296 A1 | 12/2012 |
| CA | 2797359 A1 | 11/2011 |

(Continued)

OTHER PUBLICATIONS

"InstaTrak 3500 Plus. Applications: ENT. Cranial." http://www.gehealthcare/usen/xr/surgery/products/nav.html (printed Dec. 14, 2009).

(Continued)

*Primary Examiner* — Long V Le
*Assistant Examiner* — Angela M Hoffa
(74) *Attorney, Agent, or Firm* — Harness, Dickey

(57) ABSTRACT

An instrument tracking device for cooperating with an instrument during a surgical procedure where the instrument has an elongated body extending along a first longitudinal axis and including a working member at a distal tip includes a body having a distal end and a proximal end. An opening can be formed through the body along a second longitudinal axis. The opening can define a passthrough in the body from the distal end to the proximal end. A first tracking coil can be disposed in the body and can define a first tracking coil axis that is substantially coaxial with the second longitudinal axis of the body. A connection mechanism cooperates between the elongated housing and the body that secures the body to the elongated housing of the instrument upon passing at least a portion of the elongated housing through the passthrough of the body in an assembled position.

22 Claims, 8 Drawing Sheets

(51) Int. Cl.
*A61B 5/06* (2006.01)
*A61B 8/08* (2006.01)
*A61B 17/16* (2006.01)
*A61B 17/32* (2006.01)

(52) U.S. Cl.
CPC .............. *A61B 17/16* (2013.01); *A61B 17/32* (2013.01); *A61B 19/54* (2013.01); *A61B 2019/5251* (2013.01); *A61B 2019/5272* (2013.01); *A61B 2019/5483* (2013.01)

(56) References Cited

U.S. PATENT DOCUMENTS

| | | |
|---|---|---|
| 4,806,182 A | 2/1989 | Rydell et al. |
| 5,005,592 A | 4/1991 | Cartmell |
| 5,226,423 A | 7/1993 | Tenerz et al. |
| 5,391,199 A | 2/1995 | Ben-Haim |
| 5,443,489 A | 8/1995 | Ben-Haim |
| 5,591,141 A | 1/1997 | Nettekoven |
| 5,592,939 A | 1/1997 | Martinelli |
| 5,740,808 A | 4/1998 | Panescu et al. |
| 5,762,637 A | 6/1998 | Berg et al. |
| 5,840,024 A | 11/1998 | Taniguchi et al. |
| 5,913,820 A | 6/1999 | Bladen et al. |
| 5,938,602 A | 8/1999 | Lloyd |
| 5,963,120 A | 10/1999 | Zaviska |
| 5,983,126 A | 11/1999 | Wittkampf |
| 6,021,343 A | 2/2000 | Foley et al. |
| 6,106,486 A | 8/2000 | Tenerz et al. |
| 6,201,387 B1 | 3/2001 | Govari |
| 6,235,038 B1 | 5/2001 | Hunter et al. |
| 6,253,770 B1 | 7/2001 | Acker et al. |
| 6,254,600 B1 | 7/2001 | Willink et al. |
| 6,332,891 B1 | 12/2001 | Himes |
| 6,336,906 B1 | 1/2002 | Hammarstrom et al. |
| 6,348,058 B1 | 2/2002 | Melkent et al. |
| 6,381,485 B1 | 4/2002 | Hunter et al. |
| 6,427,079 B1 | 7/2002 | Schneider et al. |
| 6,434,507 B1 | 8/2002 | Clayton et al. |
| 6,474,341 B1 | 11/2002 | Hunter et al. |
| 6,478,802 B2 | 11/2002 | Kienzle, III et al. |
| 6,556,857 B1 | 4/2003 | Estes et al. |
| 6,610,066 B2 | 8/2003 | Dinger et al. |
| 6,615,155 B2 | 9/2003 | Gilboa |
| 6,616,651 B1 | 9/2003 | Stevens |
| 6,687,531 B1 | 2/2004 | Ferre et al. |
| 6,689,049 B1 | 2/2004 | Miyagi et al. |
| 6,695,764 B2 | 2/2004 | Silverman et al. |
| 6,747,539 B1 | 6/2004 | Martinelli |
| 6,796,988 B2 | 9/2004 | Melkent et al. |
| 6,833,814 B2 | 12/2004 | Gilboa et al. |
| 6,926,674 B2 | 8/2005 | Tenerz et al. |
| 6,940,941 B2 | 9/2005 | Gregerson et al. |
| 6,977,575 B2 | 12/2005 | Bernier |
| 6,980,849 B2 | 12/2005 | Sasso |
| 6,993,374 B2 | 1/2006 | Sasso |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,118,378 B1 | 10/2006 | Karapetyan |
| 7,166,114 B2 | 1/2007 | Moctezuma De La Barrera et al. |
| 7,188,998 B2 | 3/2007 | Gregerson et al. |
| 7,226,456 B2 | 6/2007 | O'Neil et al. |
| 7,346,417 B2 | 3/2008 | Luth et al. |
| 7,366,562 B2 | 4/2008 | Dukesherer et al. |
| 7,410,480 B2 | 8/2008 | Muni et al. |
| 7,462,175 B2 | 12/2008 | Chang et al. |
| 7,500,971 B2 | 3/2009 | Chang et al. |
| 7,537,594 B2 | 5/2009 | Sartor |
| 7,559,137 B2 | 7/2009 | Beer et al. |
| 7,604,609 B2 | 10/2009 | Jervis |
| 7,625,617 B1 | 12/2009 | Anderson et al. |
| 7,629,015 B2 | 12/2009 | Anderson et al. |
| 7,637,896 B2 | 12/2009 | Voegele et al. |
| 7,647,083 B2 | 1/2010 | Al-Ali et al. |
| 7,697,972 B2 | 4/2010 | Verard et al. |
| 7,751,865 B2 | 7/2010 | Jascob et al. |
| 7,763,035 B2 | 7/2010 | Melkent et al. |
| 7,774,933 B2 | 8/2010 | Wilson et al. |
| 7,797,032 B2 | 9/2010 | Martinelli et al. |
| 7,818,044 B2 | 10/2010 | Dukesherer et al. |
| 7,840,253 B2 | 11/2010 | Tremblay et al. |
| 7,844,319 B2 | 11/2010 | Susil et al. |
| 7,971,341 B2 | 7/2011 | Dukesherer et al. |
| 7,979,032 B2 | 7/2011 | Lomnitz |
| 8,075,969 B2 | 12/2011 | Anderson et al. |
| 8,086,298 B2 | 12/2011 | Whitmore, III et al. |
| 8,105,339 B2 | 1/2012 | Melkent et al. |
| 8,147,486 B2 | 4/2012 | Honour et al. |
| 8,239,001 B2 | 8/2012 | Verard et al. |
| 8,251,949 B2 | 8/2012 | Warnack |
| 8,255,027 B2 | 8/2012 | Al-Ali et al. |
| 8,504,139 B2 | 8/2013 | Jacobsen et al. |
| 8,644,907 B2 * | 2/2014 | Hartmann et al. ............. 600/424 |
| 8,648,605 B2 | 2/2014 | Nakamura et al. |
| 8,674,694 B2 | 3/2014 | Hyde et al. |
| 8,862,204 B2 | 10/2014 | Sobe et al. |
| 2001/0034549 A1 | 10/2001 | Bartholf et al. |
| 2002/0165448 A1 | 11/2002 | Ben-Haim et al. |
| 2003/0050552 A1 | 3/2003 | Vu |
| 2003/0187347 A1 | 10/2003 | Nevo et al. |
| 2004/0116803 A1 | 6/2004 | Jascob et al. |
| 2004/0199072 A1 | 10/2004 | Sprouse et al. |
| 2004/0215071 A1 | 10/2004 | Frank et al. |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0060885 A1 | 3/2005 | Johnson et al. |
| 2005/0085715 A1 | 4/2005 | Dukesherer et al. |
| 2005/0085720 A1 | 4/2005 | Jascob et al. |
| 2005/0105212 A1 | 5/2005 | Sato |
| 2005/0154294 A1 | 7/2005 | Uchiyama et al. |
| 2005/0171508 A1 | 8/2005 | Gilboa |
| 2005/0215922 A1 | 9/2005 | Tsonton et al. |
| 2005/0222554 A1 | 10/2005 | Wallace et al. |
| 2006/0004286 A1 | 1/2006 | Chang et al. |
| 2006/0025677 A1 | 2/2006 | Verard et al. |
| 2006/0036189 A1 | 2/2006 | Martinelli et al. |
| 2006/0084867 A1 | 4/2006 | Tremblay et al. |
| 2006/0142656 A1 | 6/2006 | Malackowski et al. |
| 2006/0206039 A1 | 9/2006 | Wilson et al. |
| 2006/0206170 A1 | 9/2006 | Denker et al. |
| 2006/0224142 A1 | 10/2006 | Wilson et al. |
| 2006/0229624 A1 | 10/2006 | May et al. |
| 2006/0235314 A1 | 10/2006 | Migliuolo et al. |
| 2007/0088416 A1 | 4/2007 | Atalar et al. |
| 2007/0157828 A1 | 7/2007 | Susel et al. |
| 2007/0197899 A1 | 8/2007 | Ritter et al. |
| 2007/0208252 A1 | 9/2007 | Makower |
| 2007/0220746 A1 | 9/2007 | Anderson et al. |
| 2007/0225595 A1 | 9/2007 | Malackowski et al. |
| 2007/0255132 A1 | 11/2007 | Shalgi et al. |
| 2008/0097195 A1 | 4/2008 | Urquhart et al. |
| 2008/0097347 A1 | 4/2008 | Arvanaghi |
| 2008/0119727 A1 | 5/2008 | Barbagli et al. |
| 2008/0119919 A1 | 5/2008 | Atalar et al. |
| 2008/0132909 A1 | 6/2008 | Jascob et al. |
| 2008/0171934 A1 | 7/2008 | Greenan et al. |
| 2008/0171937 A1 | 7/2008 | Dukesherer et al. |
| 2008/0172069 A1 | 7/2008 | Dukesherer et al. |
| 2008/0228195 A1 | 9/2008 | von Jako et al. |
| 2009/0088728 A1 | 4/2009 | Dollar et al. |
| 2009/0118742 A1 | 5/2009 | Hartmann et al. |
| 2009/0171187 A1 | 7/2009 | Gerhart et al. |
| 2009/0204023 A1 | 8/2009 | Goldenberg |
| 2009/0209947 A1 | 8/2009 | Gordin et al. |
| 2010/0063383 A1 | 3/2010 | Anderson et al. |
| 2010/0081965 A1 | 4/2010 | Mugan et al. |
| 2010/0130852 A1 | 5/2010 | Neidert et al. |
| 2010/0185083 A1 | 7/2010 | Neidert et al. |
| 2010/0210939 A1 | 8/2010 | Hartmann et al. |
| 2010/0228117 A1 | 9/2010 | Hartmann |
| 2010/0234724 A1 | 9/2010 | Jacobsen et al. |
| 2010/0253361 A1 | 10/2010 | Nakamura et al. |

(56) References Cited

U.S. PATENT DOCUMENTS

| | | | |
|---|---|---|---|
| 2010/0280363 A1 | 11/2010 | Skarda et al. | |
| 2010/0331763 A1 | 12/2010 | Wilson et al. | |
| 2011/0014705 A1 | 1/2011 | Leach et al. | |
| 2011/0060214 A1 | 3/2011 | Makower | |
| 2011/0066029 A1 | 3/2011 | Lyu et al. | |
| 2011/0251519 A1 | 10/2011 | Romoscanu | |
| 2011/0258842 A1 | 10/2011 | Dukesherer et al. | |
| 2011/0270081 A1 | 11/2011 | Burg et al. | |
| 2012/0172696 A1 | 7/2012 | Kallback et al. | |
| 2012/0197108 A1 | 8/2012 | Hartmann et al. | |
| 2012/0197109 A1 | 8/2012 | Hartmann et al. | |
| 2012/0197110 A1 | 8/2012 | Hartmann et al. | |
| 2012/0245665 A1 | 9/2012 | Friedman et al. | |
| 2012/0283570 A1 | 11/2012 | Tegg | |
| 2013/0066194 A1 | 3/2013 | Seter et al. | |
| 2013/0137954 A1 | 5/2013 | Jacobsen et al. | |
| 2014/0012130 A1* | 1/2014 | Jacobsen et al. | 600/424 |
| 2014/0148692 A1* | 5/2014 | Hartmann et al. | 600/424 |
| 2014/0158555 A1 | 6/2014 | Nakamura et al. | |
| 2014/0276004 A1* | 9/2014 | Strupeck et al. | 600/424 |
| 2015/0005625 A1 | 1/2015 | Sobe et al. | |

FOREIGN PATENT DOCUMENTS

| | | |
|---|---|---|
| DE | 102009030731 A1 | 12/2010 |
| EP | 0425319 A2 | 5/1991 |
| EP | 1302172 A1 | 4/2003 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2123220 A1 | 11/2009 |
| EP | 2563260 A2 | 3/2013 |
| JP | 03-207344 B2 | 9/2001 |
| JP | 2007-527296 A | 9/2007 |
| JP | 2008194475 A | 8/2008 |
| JP | 2010082446 A | 4/2010 |
| WO | WO-9632060 A1 | 10/1996 |
| WO | WO-9729682 A1 | 8/1997 |
| WO | WO-9729684 A1 | 8/1997 |
| WO | WO-9940856 A1 | 8/1999 |
| WO | WO-0038571 A1 | 7/2000 |
| WO | WO-0134050 A2 | 5/2001 |
| WO | WO-2006096685 A1 | 9/2006 |
| WO | WO-2006116597 A2 | 11/2006 |
| WO | WO-2008105874 A1 | 9/2008 |
| WO | WO-2009152486 A1 | 12/2009 |
| WO | WO-2010049834 A1 | 5/2010 |
| WO | WO-2010124285 A1 | 10/2010 |
| WO | WO-2010144419 A2 | 12/2010 |
| WO | WO-2011137301 A2 | 11/2011 |
| WO | WO-2012103304 | 8/2012 |
| WO | WO-2012103304 A1 | 8/2012 |
| WO | WO-2012103407 A1 | 8/2012 |
| WO | WO-2012103410 A1 | 8/2012 |
| WO | WO-2013062869 A1 | 5/2013 |

OTHER PUBLICATIONS

"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).

"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).

"InstaTrak® Image Guided Sinus Surgery, Introduction to the InstaTrak System." Sinus-Clear.com http://www.sinus-clear.com/instatrak.htm (printed Dec. 14, 2009).

"Mayfield® Skull Clamps and Headrest Systems," Mayfield® Surgical Devices Product Index, pp. 1-6, Dec. 2004 Integra LifeSciences Corporation.

"Medtronic O-Arm Multi-Dimensional Surgical Imaging System"; Brochure, 24pp, 2009.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"The doctor can see you now" brochure. GE Medical Systems (2003) General Electric Company.

"TREON, StealthStation," brochure, Medtronic Surgical Navigation Technologies (2001) 8 pages.

Acclarent™ "Instructions for Use. Balloon Sinuplasty™ System. Relieva™ Devices, ReliENT™ Navigation System, and OptiLINK™ Extension." (Aug. 21, 2009) pp. 1-13.

Acclarent™ "Instructions for Use. Relieva Flex™ Sinus Guide Catheter, Relieva® Sinus Guide Catheter." (Sep. 19, 2009) pp. 1-6.

Examiner's Report dated Dec. 18, 2013 for Canadian Application No. 2,797,359 claiming benefit of U.S. Appl. No. 13/097,243, filed Apr. 29, 2011.

http://oxforddictionaries.com/definition/english/barrel (accessed Dec. 3, 2012).

International Preliminary Report on Patentability mailed Aug. 8, 2013 for PCT/US2012/022676 claiming benefit of U.S. Appl. No. 13/016,740, filed Jan. 28, 2011.

International Preliminary Report on Patentability mailed Aug. 8, 2013 for PCT/US2012/022840 claiming benefit of U.S. Appl. No. 13/016,762, filed Jan. 28, 2011.

International Preliminary Report on Patentability mailed Aug. 8, 2013 for PCT/US2012/022846 claiming benefit of U.S. Appl. No. 13/016,765, filed Jan. 28, 2011.

International Preliminary Report on Patentability mailed Nov. 15, 2012 for PCT/US2011/34475 claiming benefit of U.S. Appl. No. 13/097,243, filed Apr. 29, 2011.

International Search Report and Written Opinion mailed Feb. 6, 2013 for PCT/US2012/061086 claiming benefit of U.S. Appl. No. 13/281,001, filed Oct. 25, 2011.

International Search Report and Written Opinion mailed Jul. 6, 2012 for PCT/US2012/022840 claiming benefit to U.S. Appl. No. 13/016,762, filed Jan. 28, 2011.

International Search Report and Written Opinion mailed May 9, 2012 for PCT/US2012/022676 claiming benefit of U.S. Appl. No. 13/016,740, filed Jan. 28, 2011.

International Search Report and Written Opinion mailed May 9, 2012 for PCT/US2012/022846 claiming benefit of U.S. Appl. No. 13/016,765, filed Jan. 28, 2011.

International Search Report and Written Opinion mailed Oct. 31, 2011, claiming benefit of U.S. Appl. No. 13/097,243, filed Apr. 29, 2011.

Invitation to Pay Additional Fees mailed Dec. 17, 2012 for PCT/US2012/061086 claiming benefit of U.S. Appl. No. 13/281,001, filed Oct. 25, 2011.

Invitation to Pay Additional Fees mailed Jul. 25, 2011, claiming benefit of U.S. Appl. No. 13/097,243, filed Apr. 29, 2011.

Invitation to Pay Additional Fees mailed May 8, 2012 for PCT/US2012/022840 claiming benefit of U.S. Appl. No. 13/016,762, filed Jan. 28, 2011.

Japanese Office Action dated Jan. 7, 2014 for Japan Application No. 2013-508273 claiming benefit of U.S. Appl. No. 13/097,243, filed Apr. 29, 2011.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

"Flexible electronics," Dec. 19, 2012, XP055112518, en.wikipedia.org. Retrieved form the Internet: <URL:http://en.wikipedia.org/w/index.php?title=Flexible_electronics&oldid=528841651>.[retrieved on Apr. 7, 2014]. (6 sheets).

"Flexible Printed Circuit Manufacturer—Capabilities," Aug. 16, 2012, XP055112534, fpcexpress.com. Retrieved from the Internet: URL: <http://web.archive.org/web/20120816030431/http://fpcexpress.com/capabilities.html>.[retrieved on Apr. 7, 2014][retrieved on May 8, 2014]. (3 sheets).

"Minco Bulletin FC-3," Jul. 31, 2002. XP055115671, Retrieved from the Internet: <URL:http://www.temflexcontrols.com/pdf/fc3.pdf> [retrieved on Apr. 29, 2014]. (1 sheet).

(56) References Cited

OTHER PUBLICATIONS

"Sectional design standard for flexible printed boards," Internet Citation, Nov. 30, 1998, pp. 1-35, XP002691487, Retrieved form the Interent: <URL:http://222.184.16.210/smt/tzxt/bz/IPC-2223.pdf>. [retrieved on Feb. 1, 2013].
International Preliminary Report on Patentability and Written Opinion mailed May 8, 2014 for PCT/US2012/061086 claiming benefit of U.S. Appl. No. 13/281,001, filed Oct. 25, 2011.
International Search Report and Written Opinion mailed Apr. 23, 2014 for PCT/US2014/012786 claiming benefit of U.S. Appl. No. 13/748,150, filed Jan. 23, 2013.
International Search Report and Written Opinion mailed May 12, 2014 for PCT/US2014/012967 claiming benefit of U.S. Appl. No. 13/751,032, filed Jan. 25, 2013.
International Preliminary Report on Patentability and Written Opinion mailed Sep. 22, 2011 for PCT/US2010/026655 claiming benefit of U.S. Appl. No. 12/400,451, filed Mar. 10, 2009.
International Search Report mailed Jul. 15, 2010 for PCT/US2010/026655 claiming benefit of U.S. Appl. No. 12/400,451, filed Mar. 10, 2009.
Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
International Search Report and Written Opinion mailed Oct. 27, 2014 for PCT/US2014/028100 claiming benefit of U.S. Appl. No. 14/209,696, filed Mar. 13, 2014.
Invitation to Pay Additional Fees and Where Applicable, Protest Fee mailed Aug. 14, 2014 for PCT/US2014/028100 claiming benefit of U.S. Appl. No. 14/209,696, filed Mar. 13, 2014.
Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
Communication pursuant to Article 94(3) EPC for European Application No. 12703208.4-1654 dated Apr. 24, 2015.
International Preliminary Report on Patentability and Written Opinion mailed on Aug. 6, 2015 for PCT/US2014/012786 claiming benefit of U.S. Appl. No. 13/748,150, filed on Jan. 23, 2012.
International Preliminary Report on Patentability and Written Opinion mailed on Aug. 6, 2015 for PCT/US2014/012967 claiming benefit of U.S. Appl. No. 13/751,032, filed on Jan. 25, 2013.
International Preliminary Report on Patentability and Written Opinion mailed Sep. 24, 2015 for PCT/US2014/028100 claiming benefit to U.S. Appl. No. 14/209,696, filed Mar. 13, 2014.
International Preliminary Report on Patentability mailed Oct. 27, 2015 for PCT/US2014/034022 claiming benefit of U.S. Appl. No. 13/871,616, filed Apr. 26, 2013.

* cited by examiner

NAVIGATING A SURGICAL INSTRUMENT

CROSS-REFERENCE TO RELATED APPLICATIONS

This application is a continuation of U.S. patent application Ser. No. 12/400,951 filed on Mar. 10, 2009. The disclosure of the above application is incorporated herein by reference.

FIELD

The present disclosure relates generally to image-guided surgery systems, and particularly to a removable electromagnetic instrument tracking device that selectively couples with a surgical handpiece.

BACKGROUND

The statements in this section merely provide background information related to the present disclosure and may not constitute prior art.

Surgical procedures can be performed on anatomies such as the human anatomy for providing a therapy to the anatomy. One area of surgery includes procedures performed on facial cavities of a patient such as on the ear, nose or throat (ENT). In such a procedure, a working member such as a shaver, bur, or other tool connected to an instrument (e.g., a handpiece) may be inserted into such a cavity to perform a shaping procedure for example. As it is desirable to minimize trauma produced by such procedures, it is favorable to avoid any supplemental incisions or other axis portals to be formed in the patient tissue.

Because the viewing angle of a surgeon at the area of interest can be obscured by the surrounding tissue of the cavity, the ability of a surgeon to effectively apply a therapy can be reduced. Therefore, it is desirable to provide a mechanism so that a surgeon can provide a therapy without minimization or reduction of effectiveness of the procedure or in viewing the area to apply the therapy. Navigation of instruments relative to the anatomy can be used.

In some navigation systems, instruments are provided with tracking devices. Sometimes however such tracking devices can be difficult to manipulate or cumbersome to the instrument. In other instances, the tracking devices can protrude a significant distance from the instrument and interfere with a surgeon's sight line. Other tracking devices fail to provide accurate positional information in 3-dimensional space or may be susceptible to electromagnetic interference because of metal objects.

SUMMARY

An instrument tracking device for cooperating with an instrument during a surgical procedure where the instrument has an elongated body extending along a first longitudinal axis and including a working member at a distal tip includes a body having a distal end and a proximal end. An opening can be formed through the body along a second longitudinal axis. The opening can define a passthrough in the body from the distal end to the proximal end. A first tracking coil can be disposed in the body and can define a first tracking coil axis that is substantially coaxial with the second longitudinal axis of the body. The first tracking coil can generate an output signal indicative of a position of the working member. A connection mechanism cooperates between the elongated housing and the body that secures the body to the elongated housing of the instrument upon passing at least a portion of the elongated housing through the passthrough of the body in an assembled position.

According to additional features, the first tracking coil can define a first tracking coil plane. A second tracking coil can be disposed in the body. The second tracking coil can define a second tracking coil plane that is substantially orthogonal relative to the first tracking coil plane. The second and third coils can be disposed in the body at a radially offset position relative to the first tracking coil. The first and second longitudinal axes can be collinear in the assembled position.

According to other features, a third tracking coil can be disposed in the body. The third tracking coil can define a third tracking coil plane that is substantially orthogonal to the first and second tracking coil planes. The second tracking coil can define a second tracking coil axis. The third tracking coil can define a third tracking coil axis. The second and third tracking coil axes can be substantially perpendicular.

In one configuration, the body can include a conical section that extends radially outwardly from the distal end to the proximal end. The second and third tracking coils can be offset toward the proximal end of the body relative to the first tracking coil. The body can include a pair of lobes that project radially from the proximal end of the body and alternately accommodate the second and third coils, respectively. The body can include an extension portion formed intermediate of the pair of lobes that accommodates a wire harness. According to one configuration, the body can comprise a base having the first, second and third tracking coils disposed therein and a cap that covers the base. The base and the cover can be formed of plastic.

According to one configuration, the body can be low profile relative to the instrument, such that an outermost distance of the body measured radially from the first tracking coil axis is less than three times an inner diameter of the opening. The instrument can comprise a surgical handpiece. The working member can comprise a blade or a bur. In one configuration, the body can be removably attached to the longitudinal body of the instrument with an adhesive. In one example, the working member can be removable from the body. In another example, the working member can be fixed and non-removable relative to the body.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Initially, one skilled in the art will understand that the system and apparatus disclosed herein can be used in any appropriate procedure. Although a head frame is illustrated attached to a cranium and image data is illustrated for a cranium, any appropriate portion of the anatomy can be imaged. Moreover, a head frame may not be necessary and a dynamic reference frame can be attached to any appropriate structure, such as a bone screw, an adhesive base, an orifice, etc. Furthermore, the following discussion is directed toward instrumentation used during a surgical procedure focused on a sinus cavity of a patient. It will be appreciated however that the teachings may be similarly applied to other ear, nose, throat (ENT) procedures or other surgical procedures in general, such as, but not limited to anterior skull base surgery.

Figure 1:
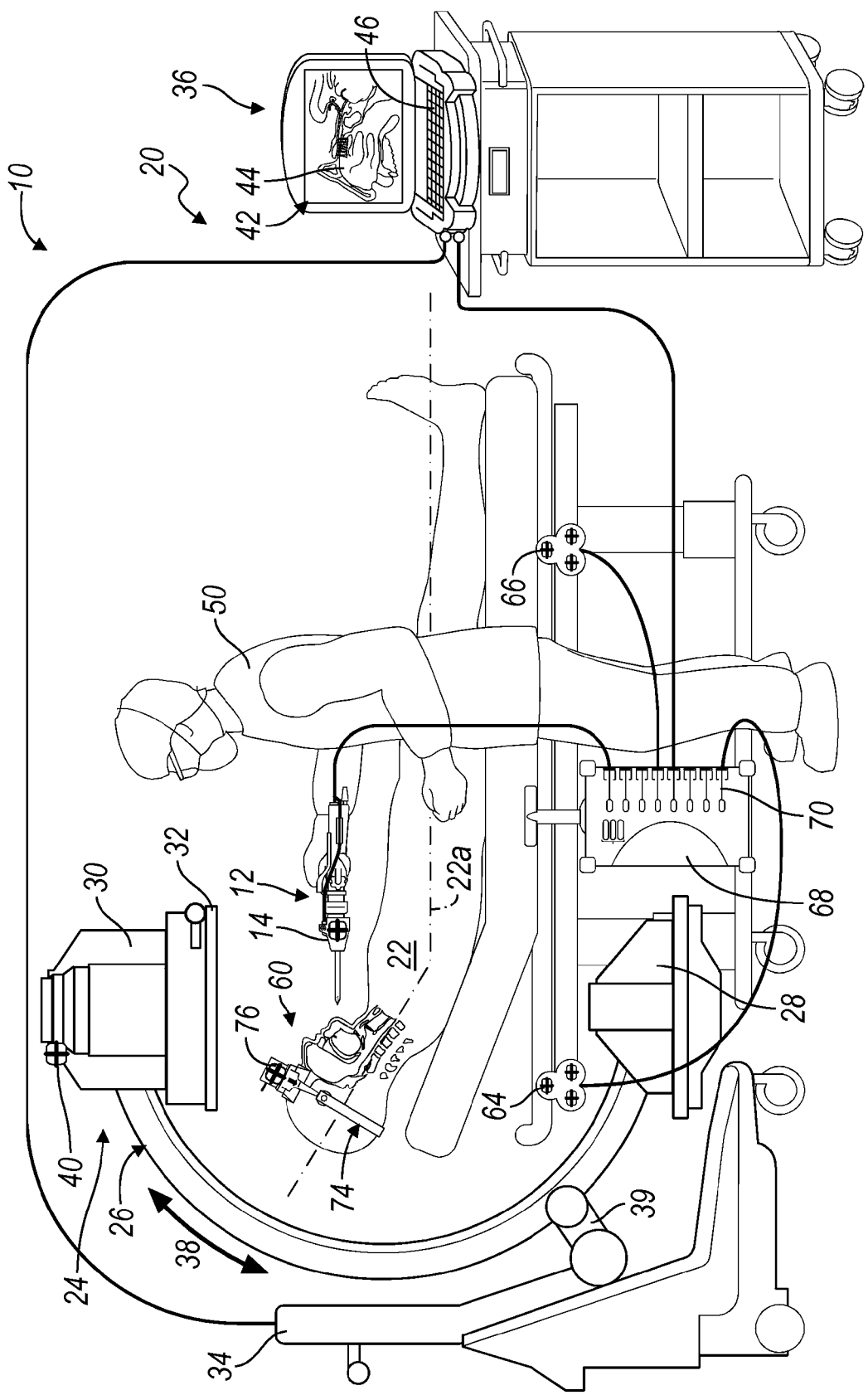
FIG. 1 is an environmental view of a surgical navigation system, according to various embodiments.

With initial reference to FIG. 1, an electromagnetic (EM) image-guided surgery system according to one example of the present teachings is shown and generally identified at reference numeral 10. The EM image-guided surgery system 10 can generally include an instrument such as a handpiece 12 having a removable EM instrument tracking device 14 configured to communicate with an exemplary navigation system 20. The navigation system 20 can be used to track the location of the handpiece 12 relative to a patient 22 to assist in a surgical procedure. As will be described in greater detail herein, the EM instrument tracking device 14 can receive a signal, transmit a signal, or combinations thereof to provide information to the navigation system 20 to determine a location of the EM instrument tracking device 14. Prior to discussing in detail the EM instrument tracking device 14 according to the present teachings, a general discussion of the exemplary navigation system 20 is warranted.

The navigation system 20 can include an imaging device 24 that is used to acquire pre-, intra-, or post-operative or real-time image data of the patient 22. The image data acquired with the imaging device 24 can be used as part of the image data in the EM image-guided surgery system 10. In addition, data from atlas models can be used to produce patient images, such as those disclosed in U.S. patent application Ser. No. 10/687,539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. The imaging device 24 is, for example, a fluoroscopic X-ray imaging device that may be configured as a C-arm 26 having an X-ray source 28, an X-ray receiving section 30, an optional calibration and tracking target 32 and optional radiation sensors. The calibration and tracking target 32 includes calibration markers (not illustrated). Image data may also be acquired using other imaging devices, such as those discussed herein.

In the exemplary configuration, the EM instrument tracking device 14 is coupled to the handpiece 12 such that the navigation system 20 can track the location of the handpiece 12, relative to a patient 22 to assist in a surgical procedure. As will be described, the EM instrument tracking device 14 can be either removably attached or fixed (non-removably attached) to the handpiece 12. It should be further noted that the EM instrument tracking device 14 can be coupled to other devices including: catheters, probes, needles, leads, implants, etc., for tracking their location with the navigation system 20. Moreover, the navigated device may be used in any region of the body. The navigation system 20 and the various devices may be used in any appropriate procedure, such as one that is generally minimally invasive, arthroscopic, percutaneous, stereotactic, or an open procedure. Although an exemplary navigation system 20 including the imaging system 24 are discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI or an O-arm™ imaging system both sold by Medtronic, Inc. It will be understood that the navigation system 20 can incorporate or be used with any appropriate preoperatively or intraoperatively acquired image data.

An optional imaging device controller 34 may control the imaging device 24, such as the C-arm 26, which can capture the x-ray images received at the X-ray receiving section 30 and store the images for later use. The controller 34 may also be separate from the C-arm 26 and can be part of or incorporated into a work station 36. The controller 34 can control the rotation of the C-arm 26. For example, the C-arm 26 can move in the direction of arrow 38 or rotate about a longitudinal axis 22a of the patient 22, allowing anterior or lateral views of the patient 22 to be imaged. Each of these movements involves rotation about a mechanical axis 39 of the C-arm 26. The movements of the imaging device 24, such as the C-arm 26 can be tracked with a tracking device 40.

In the example of FIG. 1, the longitudinal axis 22a of the patient 22 is substantially in line with the mechanical axis 39 of the C-arm 26. This enables the C-arm 26 to be rotated relative to the patient 22, allowing images of the patient 22 to be taken from multiple directions or in multiple planes. An example of a fluoroscopic C-arm X-ray device that may be used as the imaging device 24 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, intraoperative O-arm™ imaging systems, etc.

The C-arm X-ray imaging system 26 can be any appropriate system, such as a digital or CCD camera, which are well understood in the art. Two dimensional fluoroscopic images that may be taken by the imaging device 24 are captured and stored in the imaging device 24. Multiple two-dimensional images taken by the imaging device 24 may also be captured and assembled to provide a larger view or image of a whole region of the patient 22, as opposed to being directed to only a portion of a region of the patient. The multiple image data can include multiple 2D slices that are assembled into a 3D model or image.

The image data can then be forwarded from the imaging device 34 to the navigation computer and/or processor controller or work station 36 having a display device 42 to display image data 44 and a user interface 46. The work station 36 can also include or be connected to an image processor, navigation processor, and a memory to hold instruction and data. The work station 36 can include an optimization processor that assists in a navigated procedure. It will also be understood that the image data is not necessarily first retained in the controller 34, but may also be directly transmitted to the work station 36. Moreover, processing for the navigation system 20 and optimization can all be done with a single or multiple processors all of which may or may not be included in the work station 36.

The work station 36 provides facilities for displaying the image data 44 as an image on the display device 42, saving, digitally manipulating, or printing a hard copy image of the received image data. The user interface 46, which may be a keyboard, mouse, touch pen, touch screen or other suitable device, allows a physician or user 50 to provide inputs to control the imaging device 24, via the controller 34, or adjust the display settings of the display 42. The work station 36 may also direct the controller 34 to adjust the rotational axis 38 of the C-arm 26 to obtain various two-dimensional images in different planes in order to generate representative two-dimensional and three-dimensional images.

While the imaging device 24 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference), intra-vascular ultrasound (IVUS), intra-operative CT, single photo emission computed tomography (SPECT), planar gamma scintigraphy (PGS). Additional imaging systems include intraoperative MRI systems such as the PoleStar® MRI system sold by Medtronic, Inc. Further systems include the O-Arm™ imaging system sold by Medtronic, Inc. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 22. It should further be noted that the imaging device 24, as shown in FIG. 1, provides a virtual bi-plane image using a single-head C-arm fluoroscope as the imaging device 24 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, or probe introduced and advanced in the patient 22, may be superimposed in more than one view on display 42 allowing simulated bi-plane or even multi-plane views, including two and three-dimensional views.

Four-dimensional (4D) image information can be used with the navigation system 20 as well. For example, the user 50 can use a physiologic signal, which can include Heart Rate (EKG), Breath Rate (Breath Gating) and combine this data with image data 44 acquired during the phases of the physiologic signal to represent the anatomy at various stages of the physiologic cycle. For example, the brain pulses (and therefore moves) with each heartbeat. Images can be acquired to create a 4D map of the brain, onto which atlas data and representations of the instrument can be projected. This 4D data set can be matched and co-registered with the physiologic signal (EKG) to represent a compensated image within the EM image-guided surgery system 10. The image data registered with the 4D information can show the brain (or anatomy of interest) moving during the cardiac or breath cycle. This movement can be displayed on the display 42 as the image data 44.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a dynamic reference frame 60 and 4D registration techniques can help compensate for anatomic distortions during movements of the anatomy associated with normal physiologic processes.

The EM image-guided surgery system 10 includes a localizer, such as a coil array 64 and/or second tracking coil array 66, a coil array controller 68, a navigation handpiece interface 70, the handpiece 12 (e.g. catheter, needle, or instruments, as discussed herein) and the dynamic reference frame 60. The dynamic reference frame 60 can include a dynamic reference frame holder or EM, ENT head frame 74 and a removable EM, ENT patient tracker 76. In one example, the EM, ENT patient tracker 76 can be used with Synergy™ ENT software provided by Medtronic, Inc., on a computer-assisted surgery system (such as the EM image-guided surgery system 10 disclosed herein) to track the position of a patient's head during surgery. The EM, ENT head frame 74 can be mounted to the patient's forehead, such as by using an adhesive pad, a silicone pad and a frame strap. Alternatively, the head frame 74 can include a tracking device that can be formed integrally with the head frame 74.

Moreover, the DRF 60 can be provided as separate pieces and can be positioned at any appropriate position on the anatomy. For example, the ENT patient tracker 76 of the DRF can be fixed to the skin of the patient 22 with an adhesive. Also, the DRF 60 can be positioned near a leg, arm, etc. of the patient 22. Thus, the DRF 60 does not need to be provided with a head frame or require any specific base or holding portion.

The tracking devices 14, 40, 76 or any tracking device as discussed herein, can include a sensor, a transmitter, or combinations thereof. Further, the tracking devices can be wired or wireless to provide a signal emitter or receiver within the navigation system 20. For example, any or all of the tracking devices 14, 40, 76 can include an electromagnetic coil to sense a field produced by the localizing array 64, 66. Nevertheless, one will understand that the tracking device (14, 40, 76) can receive a signal, transmit a signal, or combinations thereof to provide information to the navigation system 20 to determine a location of the tracking device 14, 40, 76. Therefore, as used herein, "generating an output signal" is used to mean any combination of receiving a signal, transmitting a signal or combinations thereof. The navigation system 20 can then determine a position of the handpiece 12 or tracking device 14, 40, 76 to allow for navigation relative to the patient 22 and patient space. One suitable navigation system is disclosed in commonly owned U.S. Publication No 2008/0132909, filed Jun. 5, 2008, the contents of which are expressly incorporated herein by reference. One suitable commercially available navigation system includes "STEALTHSTATION® AXIEM™ Navigation System.

The coil arrays 64, 66 may also be supplemented or replaced with a mobile localizer. The mobile localizer may be one such as that described in U.S. patent application Ser. No. 10/941,782, filed Sep. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 14, 40, 76. The tracking device 14, 40, 76 can then transmit or receive signals based upon the transmitted or received signals from or to the array 64, 66.

Further included in the navigation system 20 may be an isolator circuit or assembly (not illustrated separately). The isolator circuit or assembly may be included in a transmission line to interrupt a line carrying a signal or a voltage to the navigation handpiece interface 70. Alternatively, the isolator circuit included in the isolator box may be included in the navigation handpiece interface 70, the handpiece 12, the dynamic reference frame 60, the transmission lines coupling the devices, or any other appropriate location. The isolator assembly is operable to isolate any of the instruments or patient coincidence instruments or portions that are in contact with the patient 22 should an undesirable electrical surge or voltage take place.

The EM image-guided surgery system 10 uses the coil arrays 64, 66 to create an electromagnetic field used for navigation. The coil arrays 64, 66 can include a plurality of coils that are each operable to generate distinct electromagnetic fields into the navigation region of the patient 22, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 64 is controlled or driven by the coil array controller 68. The coil array controller 68 drives each coil in the coil array 64 in a time division multiplex or a frequency division multiplex manner. In this regard, each coil may be driven separately at a distinct time or all of the coils may be driven simultaneously with each being driven by a different frequency.

Upon driving the coils in the coil array 64 with the coil array controller 68, electromagnetic fields are generated within the patient 22 in the area where the medical procedure is being performed, which is again sometimes referred to as patient space. The electromagnetic fields generated in the patient space induce currents in the EM instrument tracking device 14 and patient tracking device 76. These induced signals from the tracking devices 14, 40, 76 are delivered to the navigation handpiece interface 70 and subsequently forwarded to the coil array controller 68. The navigation handpiece interface 70 can also include amplifiers, filters and buffers to directly interface with the EM instrument tracking device 14 on the handpiece 12. Alternatively, the EM instrument tracking device 14, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation handpiece interface 70.

Various portions of the navigation system 20, such as the handpiece 12, or the dynamic reference frame 60, are equipped with at least one, and generally multiple, EM or other tracking devices (i.e., such as 14 and 40), that may also be referred to as localization sensors. The EM tracking devices 14, 40 can include one or more coils that are operable with the EM localizer arrays 64, 66. For example, the EM instrument tracking device 14 includes three coils as will be described. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 60 may be fixed to the patient 22 adjacent to the region being navigated so that any movement of the patient 22 is detected as relative motion between the coil array 64, 66 and the dynamic reference frame 60. The dynamic reference frame 60 can be interconnected with the patient 22 in any appropriate manner, including those discussed herein. Relative motion is forwarded to the coil array controller 68, which updates registration correlation and maintains accurate navigation, further discussed herein. The dynamic reference frame 60 may include any appropriate tracking sensor. Therefore, the dynamic reference frame 60 may also be optical, acoustic, etc. If the dynamic reference frame 60 is electromagnetic it can be configured as a pair of orthogonally oriented coils, each having the same center or may be configured in any other non-coaxial or co-axial coil configurations.

Prior to tracking the EM instrument tracking device 14, patient registration is performed. Patient registration is the process of determining how to correlate the position of the handpiece 12 relative to the patient 22 to the position on the diagnostic or image data. To register the patient 22, the physician or user 50 may use point registration by selecting and storing particular points (e.g. fiducial points) from the image data and then touching the corresponding points on the patient's anatomy (i.e., in this example various facial features such as the nose, lips, chin, cheeks or other locations near the nose) with the handpiece 12. The navigation system 20 analyzes the relationship between the two sets of points that are selected and computes a match, which correlates every point in the image data with its corresponding point on the patient's anatomy or the patient space.

The points that are selected to perform registration are the fiducial markers or landmarks, such as anatomical landmarks. Again, the landmarks or fiducial points are identifiable on the images and identifiable and accessible on the patient 22. The landmarks can be artificial landmarks that are positioned on the patient 22. The artificial landmarks, such as the fiducial markers, can also form part of the dynamic reference frame 60, such as those disclosed in U.S. Pat. No. 6,381,485, entitled "Registration of Human Anatomy Integrated for Electromagnetic Localization," issued Apr. 30, 2002, herein incorporated by reference.

The patient 22 can include one or a plurality of fiducial markers (not specifically shown) affixed to the anatomy of a patient 22, such as a cranium. It will be understood that any appropriate number of the fiducial markers can be affixed to the patient 22 and in any appropriate location. The fiducial markers can be randomly attached to the patient 22 or attached in specific locations.

The fiducial markers can include any appropriate marker to be interconnected with the patient 22. For example, the makers sold by IZI Medical Products, Baltimore, Md. can be used. The markers can include an adhesive base that is adhered to the cranium. The fiducial markers can be associated or connected to the patient 22 with an adhesive, mounting screw, clamp, etc. According to various embodiments, the fiducial markers can be attached to the patient 22 prior to acquiring image data with an adhesive in a selected manner. The fiducial markers can be placed in predetermined locations or in random locations for imaging. The fiducial marker can also include a fiducial divot or identification divot. Once registration is performed, the navigation system 20 is ready to track the EM instrument tracking device 14.

Briefly, the navigation system 20 operates as follows. The navigation system 20 creates a translation map between all points in the image data generated from the imaging device 24 which can include external and internal portions, and the corresponding points in the patient's anatomy in patient space. After this map is established, whenever the tracked handpiece 12 is used, the work station 36 in combination with the coil array controller 68 uses the translation map to identify the corresponding point on the image data or atlas model, which is displayed on display 42. This identification is known as navigation or localization. An icon representing the localized point or instruments is shown on the display 42 within several two-dimensional image planes, as well as on three and four dimensional images and models.

To enable navigation, the navigation system 20 must be able to detect both the position of the patient's anatomy and the position of the handpiece 12 (or EM instrument tracking device 14) attached to the handpiece 12. Knowing the location of these two items allows the navigation system 20 to compute and display the position of the handpiece 12 or any portion thereof (i.e., a shaver blade as will be described) in relation to the patient 22. The EM image-guided surgery system 10 is employed to track the handpiece 12 and the anatomy simultaneously.

The EM image-guided surgery system 10 essentially works by positioning the coil array 64, 66 adjacent to the patient 22 to generate a magnetic field, which can be low energy, and generally referred to as a navigation field. Because every point in the navigation field or patient space is associated with a unique field strength, the EM image-guided surgery system 10 can determine the position of the handpiece 12 by measuring the field strength at the location of the EM instrument tracking device 14. The dynamic reference frame 60 is fixed to the patient 22 to identify the location of the patient 22 in the navigation field. The EM image-guided surgery system 10 continuously recomputes or recalculates the relative position of the dynamic reference frame 60 and the handpiece 12 during localization and relates this spatial information to patient registration data to enable navigation of the handpiece 12 within and/or relative to the patient 22. Navigation can include image guidance or imageless guidance.

The navigation system 20 may also perform registration using anatomic surface information or path information as is known in the art (and may be referred to as auto-registration). The EM image-guided surgery system 10 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, now U.S. Pat. App. Pub. No. 2004/0215071, entitled "Method and Apparatus for Performing 2D to 3D Registration" filed on Aug. 20, 2003, hereby incorporated by reference.

In order to maintain registration accuracy, the navigation system 20 continuously tracks the position of the patient 22 during registration and navigation. This is because the patient 22, dynamic reference frame 60, and transmitter coil array 64, 66 may all move during the procedure, even when this movement is not desired. Alternatively the patient 22 may be held immobile once the registration has occurred, such as with a fixed head frame. Therefore, if the navigation system 20 did not track the position of the patient 22 or area of the anatomy, any patient movement after registration would result in inaccurate navigation within that image. The dynamic reference frame 60 allows the EM image-guided surgery system 10 to register and track the anatomy. Because the dynamic reference frame 60 is rigidly fixed to the patient 22, any movement of the anatomy or the coil array 64, 66 is detected as the relative motion between the coil array 64, 66 and the dynamic reference frame 60. This relative motion is communicated to the coil array controller 68, via the navigation handpiece interface 70, which updates the registration correlation to thereby maintain accurate navigation.

The navigation system 20 can be used according to any appropriate method or system. For example, image data, atlas or 3D models may be registered relative to the patient and patient space, as discussed further herein. Generally, the navigation system 20 allows the images on the display 42 to be registered and accurately display the real time location of the various instruments and other appropriate items. In addition, the handpiece 12 may be used to register the patient space to the pre-acquired image data or the atlas or 3D models. In addition, the dynamic reference frame 60 may be used to ensure that any planned or unplanned movement of the patient or the array 64, 66 is determined and used to correct the image on the display 42.

To obtain a maximum reference, it can be selected to fix the dynamic reference frame 60 in each of at least 6 degrees of freedom. Thus, the dynamic reference frame 60 can be fixed relative to axial motion X, translational motion Y, rotational motion Z, yaw, pitch, and roll relative to the portion of the patient 22 to which it is attached. Any appropriate coordinate system can be used to describe the various degrees of freedom. Fixing the dynamic reference frame relative to the patient 22 in this manner can assist in maintaining maximum accuracy of the navigation system 20.

As mentioned briefly above, the display 42 can display any appropriate type of image data 44. For example, the image data 44 can include patient specific image data that can be acquired at any appropriate time. The image data can include magnetic resonance imaging data (MRI) that can provide structural anatomical image data (i.e., such as a nasal cavity, etc.) of the patient 22. The image data 44 can be displayed on the display 42 for use during a procedure by the user 50. The display 42 can also include various atlas image data. Atlas image data can include two-dimensional image data sets, three-dimensional image data sets, and even four-dimensional image data sets that show the change of various anatomical structures over time.

Figure 2A:
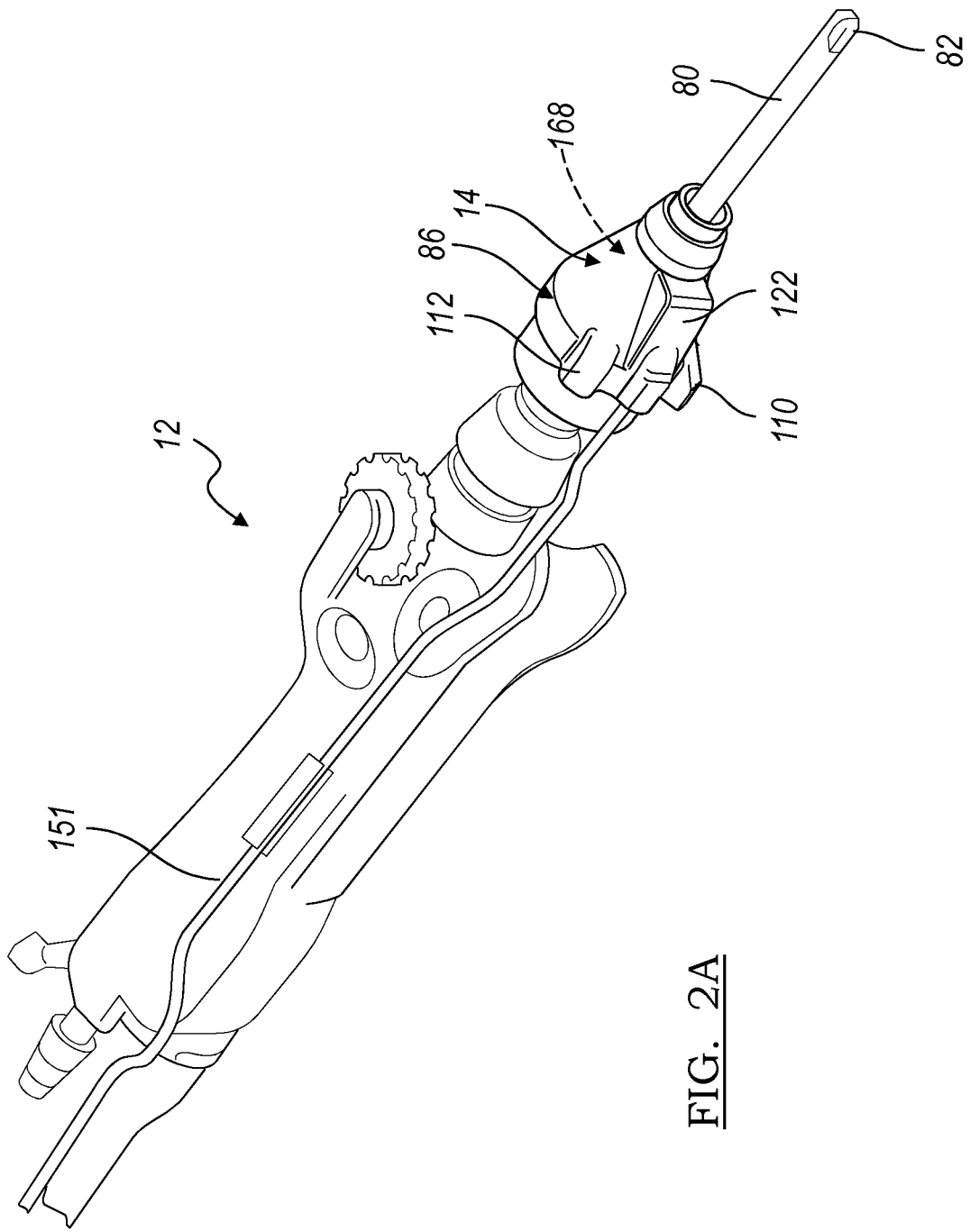
FIG. 2A is a perspective view of an exemplary handpiece having a workpiece such as a blade and shown with an electromagnetic tracking device in an assembled position on a distal end of the handpiece.

With reference now to FIG. 2A, the electromagnetic tracking device 14 is shown operatively coupled with the exemplary handpiece 12. One suitable handpiece is commercially available under the name "MENT M4 Straightshot™ Handpiece", sold by Medtronic, Inc. The handpiece 12 can include a removably (or non-removably) attached working member 80, such as a debrider, bur or blade for example. The blade 80 can include a blade tip 82. According to the exemplary embodiment, the blade tip 82 can be specifically adapted for ear, nose and throat (ENT) surgical procedures for burring or shaping various ENT cavities. While only one blade 80 is shown, the EM image-guided surgery system 10 can include a plurality of blades each having different characteristics. The location of a respective tip (i.e., 82) for each blade (i.e., 80) can be programmed into the image-guided surgery system 10, such as at a terminal connector of the handpiece 12.

Figure 2B:
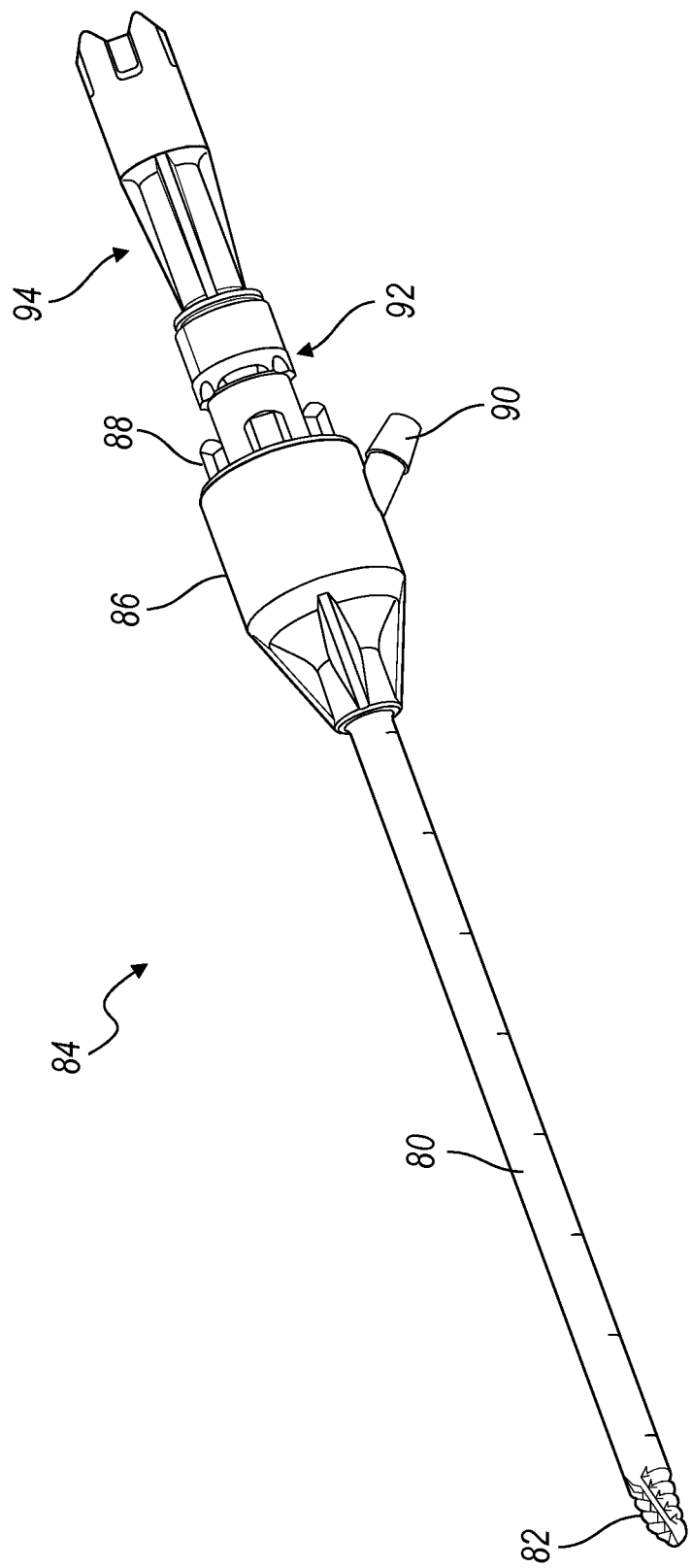
FIG. 2B is a perspective view of a blade assembly including the blade shown in FIG. 2A.

In one example, the working member 80 can be part of a blade assembly 84, FIG. 2B that is fixed to the electromagnetic tracking device 14. In another example, the working member 80 or the blade assembly 84 as a whole can be releasably coupled to the electromagnetic tracking device 14. The blade assembly 84 can include an outer hub 86 having locating tabs 88 and an aspirating port 90. A rotating hub 92 can be arranged intermediate of an inner tapered hub 94 and the outer hub 86. In an assembled position (FIG. 2A), the locating tabs 88 can engage structure (not specifically shown) on the handpiece 12. During use, rotatable motion is imparted into the rotating hub 92 for rotating within and relative to the outer hub 86.

Figure 3A:
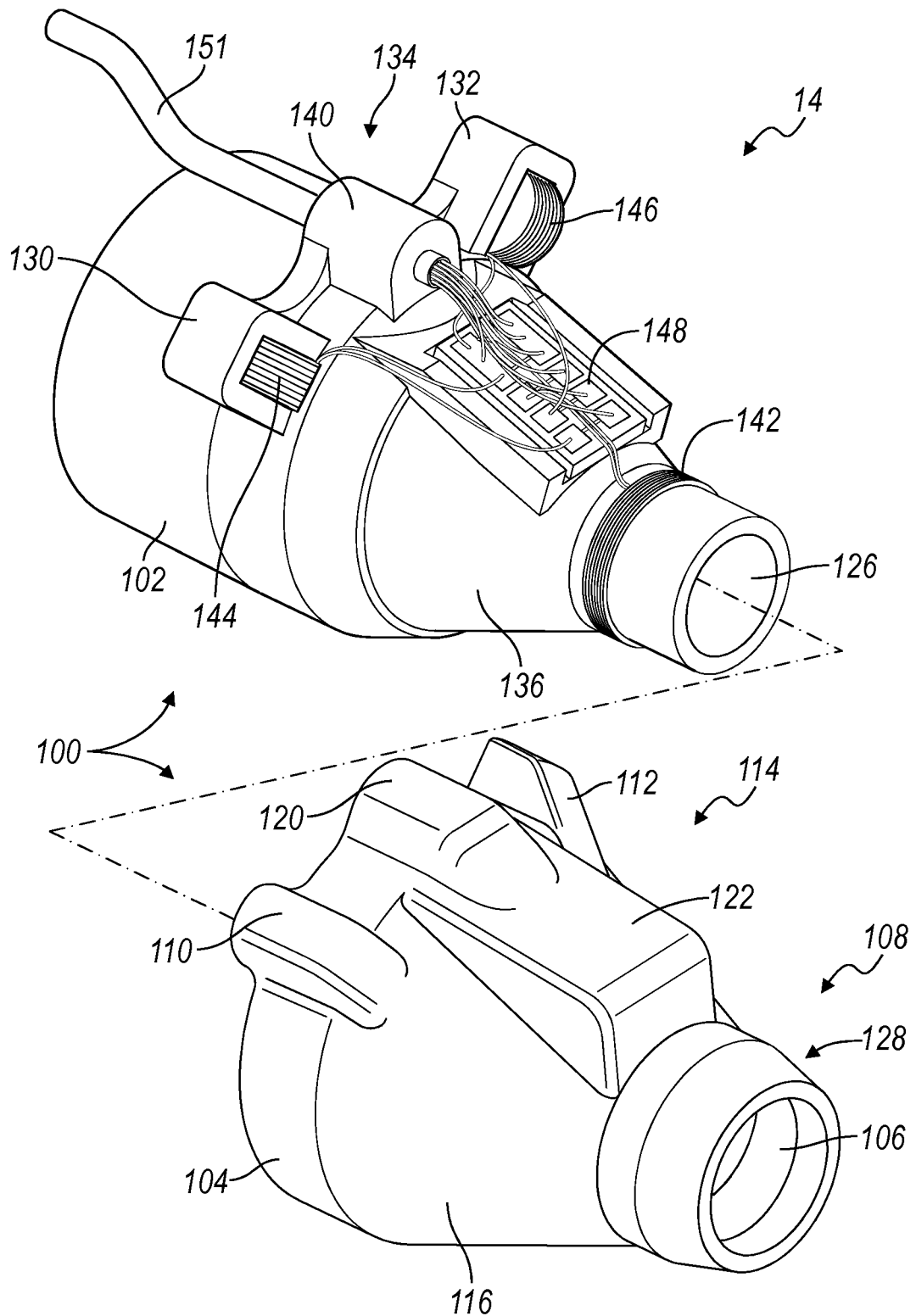
FIG. 3A is an exploded view of the instrument tracking device illustrating a body having a base and a cap.

With reference now to FIG. 3A, an exploded view of the EM instrument tracking device 14 is shown. The EM instrument tracking device 14 can generally include a body or housing 100 that comprises a base 102 and a cap 104. The cap 104 defines a cap opening 106 at a distal end 108 and a first and second lobe 110 and 112, respectively formed at a proximal end 114. The cap 104 includes a cap body 116 that defines a generally conical shape that tapers radially outwardly from the distal end 108 to the proximal end 114. A cap extension portion 120 is formed on the cap 104 generally between the first and second lobes 110 and 112. An accommodation portion 122 is formed generally on the conical section of the cap body 116 and aligned with the cap extension portion 120.

Figure 3B:
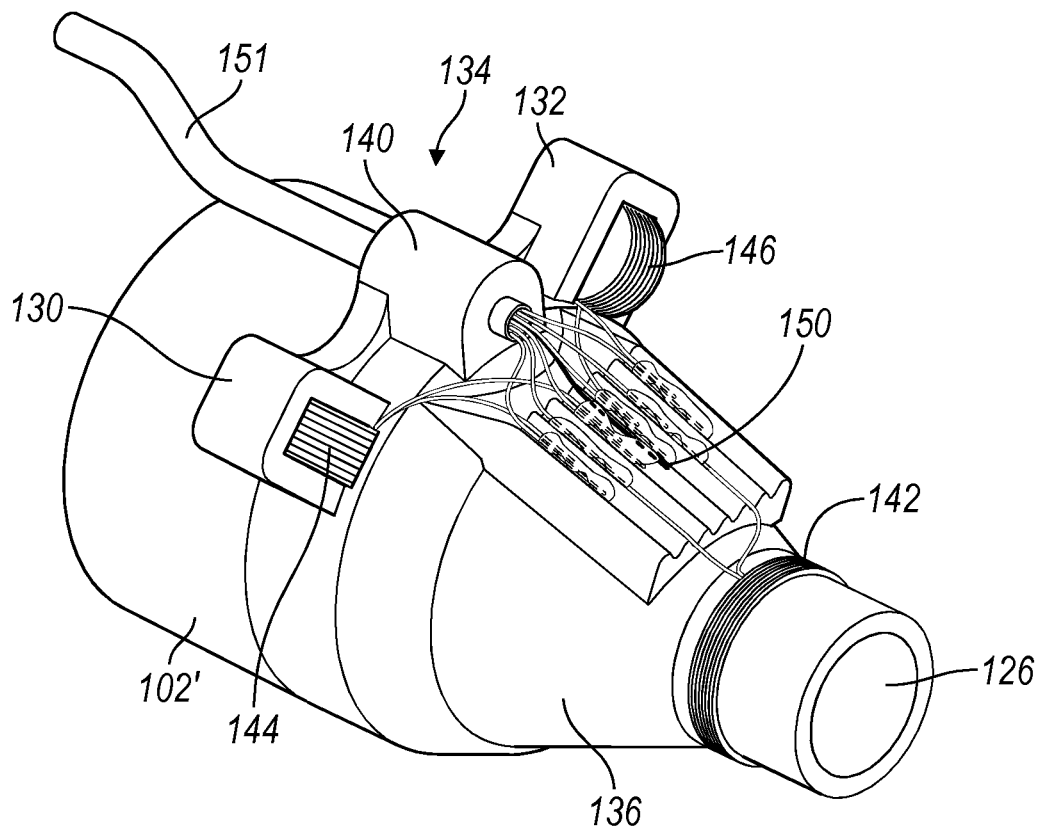
FIG. 3B is a perspective view of an instrument tracking device having a body according to additional features.
Figure 5:
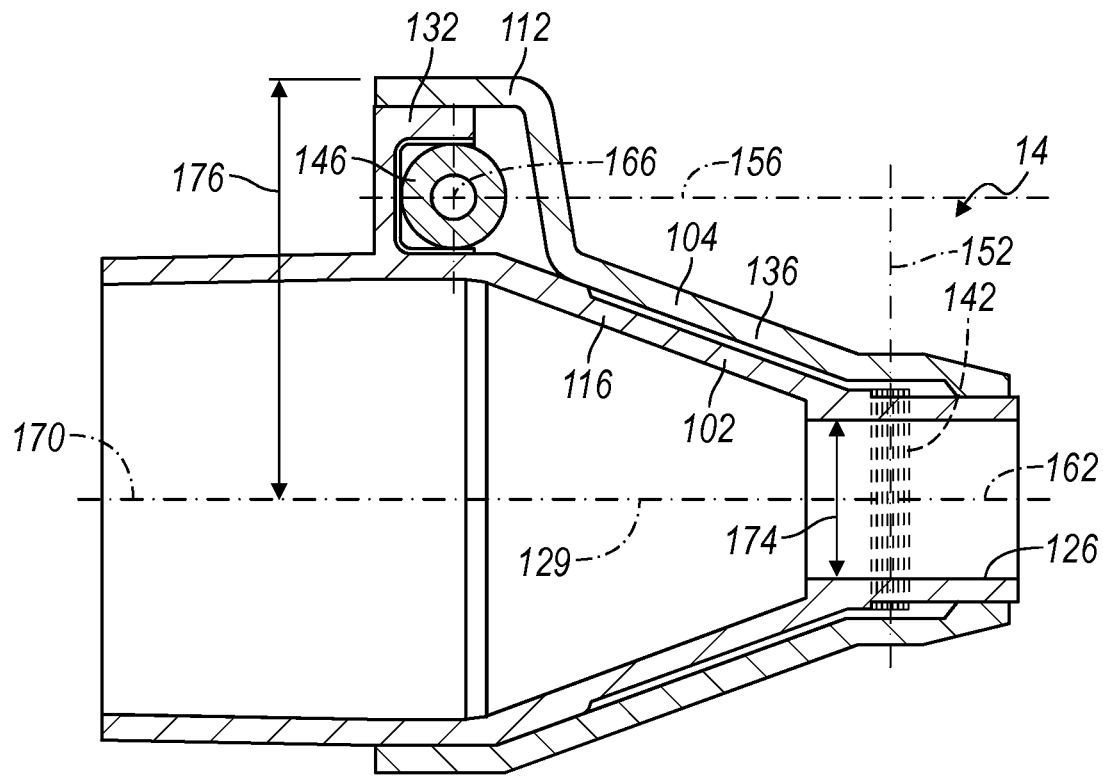
FIG. 5 is a sectional view of the instrument tracking device taken along line 5-5 of FIG. 4.

The base 102 generally includes a base opening 126 formed at a distal end 128. The base opening 126 can be concentric with a shaft of the working member 80. A base longitudinal axis 129 can be defined through the base opening 126. The longitudinal axis 170 of the handpiece 12 can be collinear with the base longitudinal axis 129 (FIG. 5). A second tracking coil support 130 and a third tracking coil support 132 can be formed at a proximal end 134 of the base 102. The base 102 generally provides a base body 136 that is in the form of a conically tapered section that expands radially outwardly from the distal end 128 of the base 102 to the proximal end 134 of the base 102. A cable support 140 is formed on the base 102 generally between the second tracking coil support 130 and the third tracking coil support 132. A first tracking coil 142 is generally disposed around the distal end 128 of the base 102 proximate to the base opening 126. A second tracking coil 144 is disposed generally within the second tracking coil support 130. A third tracking coil 146 is generally disposed within the third tracking coil support 132. The second and third tracking coils 144 and 146 are disposed radially outwardly in the body 100 relative to the first tracking coil 142. Explained differently, each of the second and third tracking coils 144 and 146 occupy a position offset radially relative to a circumference of the first tracking coil 142. Each of the first, second and third tracking coils 142, 144 and 146 are electrically connected to a terminal, such as a printed circuit board 148. A cable assembly 151 is electrically connected to the printed circuit board 148. In another example, a base 102' can be provided (FIG. 3B) where the printed circuit board 148 can be eliminated and the terminal ends of each tracking coil 142, 144 and 146 can each be electrically connected to respective wires of the cable assembly 151. A longitudinal support 150 can extend from the cable assembly 151 and be secured to the base 102'. The longitudinal support 150 can provide additional strength to the cable assembly 151 where it attaches to the base 102' to inhibit inadvertent separation of the cable assembly 151 from the base 102'. In one example, the longitudinal support 150 can be formed of Kevlar® and be adhesively attached to the base 102'. Adhesive can also be disposed in grooves of the base 102' at the respective connections between the terminal ends of the tracking coils 142, 144 and 146 and the corresponding wires of the cable assembly 151. Again, as mentioned above, the instrument tracking device 14 can communicate wirelessly to the navigation handpiece assembly.

As can be appreciated, in an assembled position (i.e., FIG. 2, 4 or 5), the cap 104 is configured to be assembled generally over the base 102. In the assembled position, the distal end 108 of the cap 104 can enclose the first tracking coil 142 disposed on the distal end 128 of the base. Similarly, the first lobe 110 of the cap 104 can enclose the second tracking coil 144 and second tracking coil support 130. The second lobe 112 of the cap 104 can enclose the third tracking coil 146 and third tracking coil support 132. The cap extension portion 120 can enclose the cable support 140. The accommodating portion 122 of the cap 104 can enclose the printed circuit board 148. In one example, a flowable adhesive, such as an epoxy can be disposed within the annular space defined between the base 102 and the cap 104 upon assembly for maintaining the cap 104 and base 102 in a secured position relative to each other. In one example, the body can be formed of molded plastic. The second and third tracking coils 144 and 146 can be molded into the base 102. Alternatively, the second and third tracking coils 144 and 146 can be glued to the base 102. Epoxy can then be urged around the second and third tracking coils 144 and 146 in the base 102 to retain the second and third tracking coils 144 and 146. The EM instrument tracking device is simple to manufacture and easy to manipulate onto and off of an instrument 12.

Figure 4:
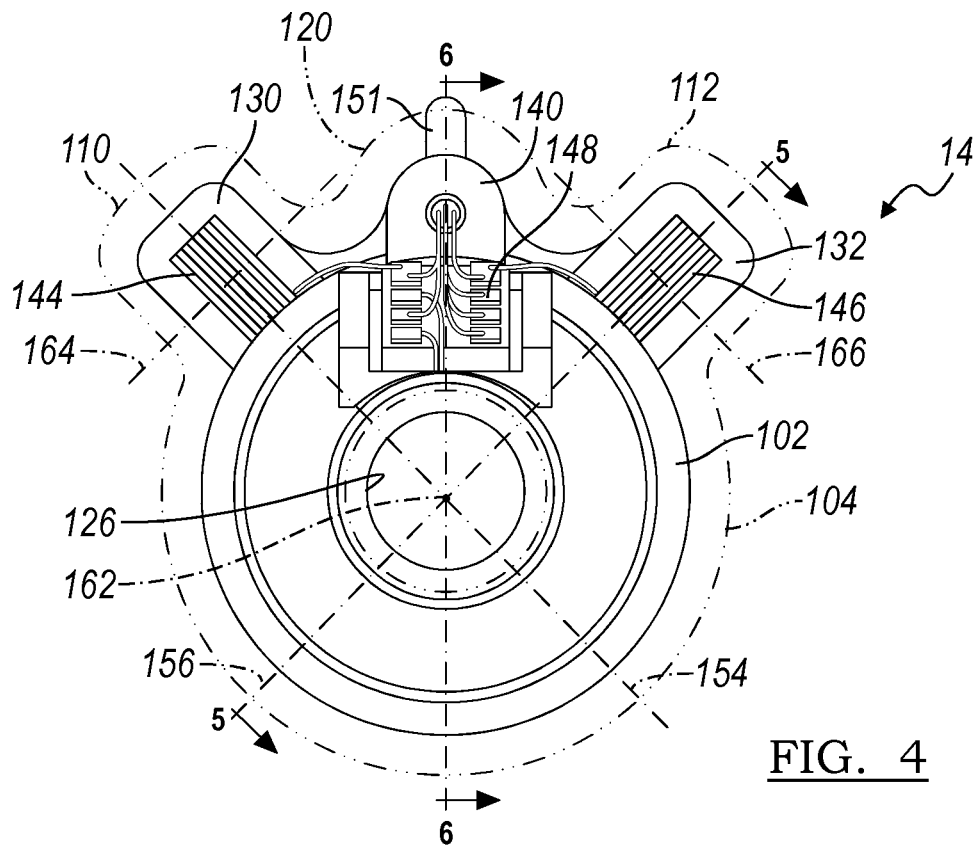
FIG. 4 is a longitudinal end view of the electromagnetic tracking device illustrated in FIG. 3A and shown with the cap in phantom.
Figure 6:
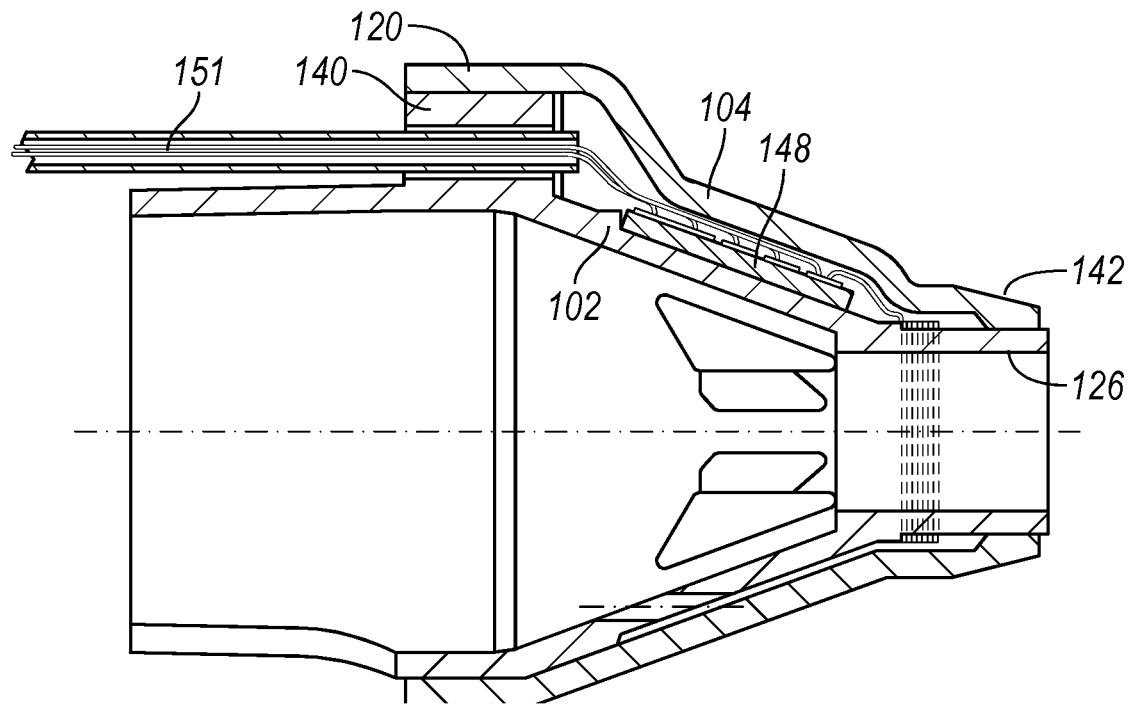
FIG. 6 is a sectional view of the electromagnetic instrument tracking device taken along line 6-6 of FIG. 4.

With additional reference now to FIGS. 4-6, additional features of the EM instrument tracking device 14 will be described. The first tracking coil 142 defines a first tracking coil plane 152. The second tracking coil 144 defines a second tracking coil plane 154. The third tracking coil 146 defines a third tracking coil plane 156. For purposes of discussion, each of the tracking coil planes 152, 154 and 156 are defined through a horizontal centerline of each of the respective tracking coils 142, 144 and 146, respectively. As illustrated in FIGS. 4 and 5, the first, second and third tracking coil planes 152, 154 and 156 are all arranged orthogonally relative to each other. Additionally, each of the first, second and third tracking coils 142, 144 and 146 define a center point (i.e., the point at which their respective axes 162, 164 and 166 intersect their respective tracking coil planes 152, 154 and 156) that do not overlap.

A first tracking coil axis 162 is defined through the first tracking coil 142. A second coil axis 164 is defined through the second tracking coil 144. A third tracking coil axis 166 is defined through the third tracking coil 146. As best illustrated in FIG. 4, the second coil axis 164 is perpendicular relative to the third coil axis 166. The first tracking coil axis 162 is collinear with a longitudinal axis 170 defined by the handpiece 12. The first tracking coil 142 is therefore arranged perpendicular relative to the longitudinal axis 170 of the handpiece 12 and concentric with the working tool axis.

In use, each of the first, second and third tracking coils 142, 144 and 146 sense the electromagnetic field produced by the coil arrays 64 and 66 and generate an output signal to the navigation handpiece interface 70 indicative of a position of the working member 80, and more specifically the blade tip 82. The specific tracking coil configuration of the present disclosure where the first, second and third tracking coils 142, 144 and 146 are positioned orthogonally relative to each other and in the specific configuration relative to the shaver reduces electromagnetic interference from the handpiece 12, which contains a substantial amount of metallic material. The tracking coils 142, 144 and 146 can provide positional, translational and rotational information (6 degrees of freedom) along the respective axes 162, 164 and 166, along the respective planes 152, 154 and 156, and around the respective axes 162, 164 and 166 for the instrument tracking device 14 as a whole.

As can be appreciated, by utilizing three tracking coils (142, 144 and 146), the EM image-guided surgery system 10 can identify the location and orientation of the set of coils 142, 144 and 146 in space and therefore can calculate the location of the blade tip 82 in 3-dimensional space. In this way, translational motion along the X, Y and Z axes as well as yaw, pitch and roll relative to the patient 22 can be determined.

As discussed above, the EM instrument tracking device 14 may be removably attached or fixed (non-removably attached) to the handpiece 12. In one example, the EM instrument tracking device 14 can be slidably advanced over a distal end of the handpiece 12 and secured with a connection mechanism 168. The connection mechanism 168 can comprise adhesive, cooperating threads, clips, snaps, fasteners or other device. Explained generally, the distal end of the handpiece 12 can be inserted through a passthrough defined by the base opening 126. In other arrangements, the EM instrument tracking device 14 may be releasably coupled to the handpiece 12, such as by way of a snap-fit connection. It is contemplated however that the EM instrument tracking device 14 can be removably affixed to the handpiece 12 by any suitable method. In general however, the EM instrument tracking device 14 is disposable and because the EM instrument tracking device 14 is removably attached to the handpiece 12, it can also be easily replaced.

The electromagnetic tracking device 14 is low profile and aesthetically pleasing to the user 50 when attached to the handpiece 12. Explained further, the respective first and second lobes 110 and 112 that accommodate the second and third tracking coils 144 and 146, respectively protrude radially outwardly a minimal distance. In one example, the base opening 126 can define a diameter 174. An outermost distance 176 can be defined from the first coil axis 162 to an outermost dimension of the body 100 (i.e., at the first or second lobe 110 or 112). The distance 176 is less than three times the diameter 174. Because the body 100 provides a low profile configuration, the user 50 is afforded a greater viewing angle at the area of interest. In this way, the body 100 is substantially free from obstructing a line of sight by the user 50 during the surgical procedure, such as down the sight line or axis of the instrument 12.

Figure 7:
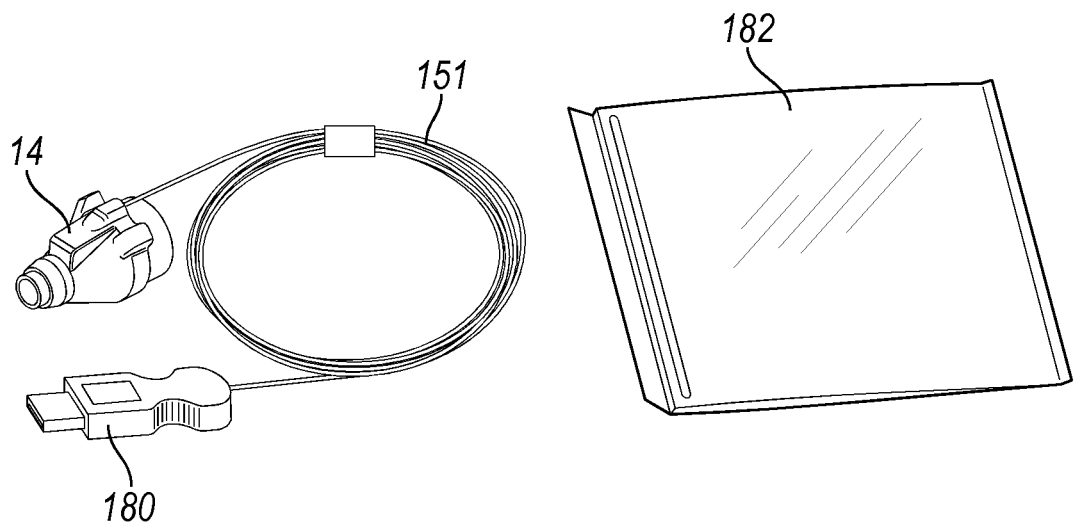
FIG. 7 is a perspective view of the electromagnetic instrument tracking device shown operatively connected with a wire harness and electrical connector and shown removed from a bag.

With reference to FIG. 7, the EM instrument tracking device 14 can be provided with the cable assembly 151 and an electrical connector 180 at an opposite end. The EM instrument tracking device 14, the cable assembly 151 and electrical connector 180 can be contained in a hermetically sealed bag 182 prior to being attached to the blade 80.

Figure 8:
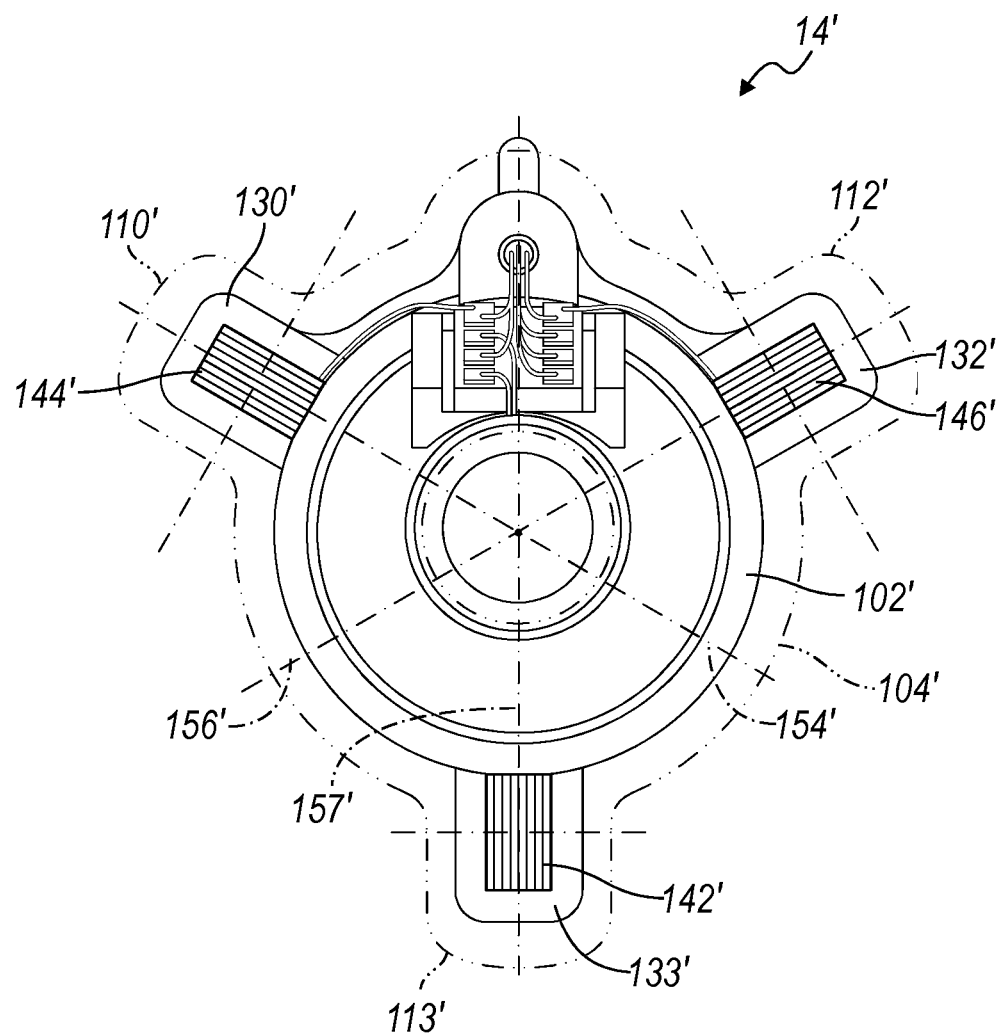
FIG. 8 is a longitudinal end view of an electromagnetic tracking device according to additional features.

In other examples, the EM instrument tracking device 14 can be provided with fewer or additional tracking coils than the three tracking coils 142, 144 and 146 described above. Moreover, the tracking coils 142, 144 and 146 can be arranged at alternate locations on the body 100. In one configuration as illustrated in FIG. 8, an EM instrument tracking device 14' can include a first tracking coil 142' that is located around the perimeter of a base 102' at a radially offset position relative to a second and third tracking coils 144' and 146'. In one example, the first tracking coil 142' can be located within a third lobe 113' of a cap 104'. The second and third tracking coils 144' and 146' can be located within a first and a second lobe 110' and 112', respectively. The first, second and third radially extending tracking coils 142', 144' and 146' can be supported by tracking coil supports 133', 130' and 132', respectively. In the example illustrated, the first, second and third tracking coils 142', 144' and 146' define tracking coil planes 157', 154' and 156' that are located at substantially 120° relative to each other substantially perpendicular to the longitudinal axis 170. Other configurations and/or radial offsets are contemplated.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. An instrument tracking device for an instrument, wherein the instrument has an elongated housing extending along a first longitudinal axis and includes a working member at a distal tip of the instrument, the instrument tracking device comprising:

a body that has an opening along a second longitudinal axis of the body, wherein the body is configured to be attached to the elongated housing such that at least a portion of the working member extends through the opening, and wherein the first longitudinal axis and the second longitudinal axis are collinear;

a first tracking coil disposed in the body and radially offset relative to the second longitudinal axis, wherein the first tracking coil defines a first tracking coil plane, wherein the second longitudinal axis line intersects the first tracking coil plane such that the second longitudinal axis extends within the first tracking coil plane, wherein the first tracking coil generates a first output signal indicative of a position of the working member relative to the first tracking coil plane;

a second tracking coil disposed in the body and radially offset relative to the second longitudinal axis, wherein the second tracking coil defines a second tracking coil plane, wherein the second longitudinal axis line intersects the second tracking coil plane such that the second longitudinal axis extends within the second tracking coil plane, wherein the second tracking coil generates a second output signal indicative of the position of the working member relative to the second tracking coil plane;

a third tracking coil disposed in the body and radially offset relative to the second longitudinal axis, wherein the third tracking coil defines a third tracking coil plane, wherein the second longitudinal axis line intersects the third tracking coil plane such that the second longitudinal axis extends within the third tracking coil plane, wherein the third tracking coil generates a third output signal indicative of the position of the working member relative to the third tracking coil plane; and wherein the first tracking coil, the second tracking coil and the third tracking coil are respectively wound about a first tracking coil axis, a second tracking coil axis and a third tracking coil axis, the first tracking coil, the second tracking coil and the third tracking coil are located at 120° positions relative to each other and about the second longitudinal axis,
the first tracking coil axis, the second tracking coil axis, and the third tracking coil axis are (i) orthogonal respectively to the first tracking coil plane, the second tracking coil plane, and the third tracking coil plane, and (ii) in a plane orthogonal to the second longitudinal axis.

2. The instrument tracking device of claim 1, wherein the first tracking coil plane, the second tracking coil plane, and the third tracking coil plane intersect each other at the second longitudinal axis.

3. The instrument tracking device of claim 1, further comprising a connection mechanism configured to secure the body to the elongated housing,
wherein at least a portion of the elongated housing extends through the opening of the body.

4. The instrument tracking device of claim 3, wherein the connection mechanism is selected from a group consisting of adhesive, cooperating threads, clips, snaps and fasteners.

5. The instrument tracking device of claim 1, wherein the body comprises:
a base having the first tracking coil, the second tracking coil and the third tracking coil disposed at least partially within the base; and
a cap that covers the base.

6. The instrument tracking device of claim 5, wherein the base and the cap are formed of plastic.

7. The instrument tracking device of claim 1, wherein:
the instrument comprises a surgical handpiece; and
the working member comprises one of a blade or a bur.

8. The instrument tracking device of claim 1, wherein:
the first tracking coil extends radially outward from the body;
the second tracking coil extends radially outward from the body; and
the third tracking coil extends radially outward from the body.

9. The instrument tracking device of claim 1, wherein:
the body includes a cable support; and
the cable support is configured to support a cable assembly external to the body and between the first tracking coil and the second tracking coil.

10. The instrument tracking device of claim 9, further comprising a printed circuit board attached to the body, wherein:
the first tracking coil, the second tracking coil, and the third tracking coil are electrically connected to the printed circuit board; and
the cable assembly is electrically connected to the printed circuit board.

11. The instrument tracking device of claim 10, wherein:
the printed circuit board comprises terminals;
the first tracking coil comprises first wires;
the second tracking coil comprises second wires;
the third tracking coil comprises third wires;
the cable assembly comprises fourth wires; and
the first wires the second wires and the third wires connect to the fourth wires at the terminals, respectively.

12. The instrument tracking device of claim 11, wherein the printed circuit board is mounted on the body distal of the first tracking coil, the second tracking coil and the third tracking coil.

13. The instrument tracking device of claim 1, further comprising:
a cable assembly mounted on the body;
a longitudinal support member mounted on the housing and comprising a plurality of grooves, wherein:
the first tracking coil comprises first wires;
the second tracking coil comprises second wires;
the third tracking coil comprises third wires;
the cable assembly comprises fourth wires; and
the first wires the second wires and the third wires connect to the fourth wires within the grooves, respectively.

14. An instrument comprising:
the instrument tracking device of claim 1;
a rotating hub connected to and proximal of the instrument tracking device; and
the working member, wherein the working member is connected to and rotated by the rotating hub.

15. The instrument of claim 14, wherein the working member comprises a blade.

16. An instrument tracking device of an instrument, wherein the instrument has an elongated housing extending along a first longitudinal axis and includes a working member at a distal tip of the instrument, the instrument tracking device comprising:
a body extending along a second longitudinal axis, wherein the body is configured to be attached to the elongated housing of the instrument;
a first tracking coil disposed on the body and radially offset relative to the second longitudinal axis, wherein the first tracking coil generates a first output signal indicative of a position of the working member relative to a first tracking coil plane;
a second tracking coil disposed on the body and radially offset relative to the second longitudinal axis, wherein the second tracking coil generates a second output signal indicative of the position of the working member relative to a second tracking coil plane;
a third tracking coil disposed on the body and radially offset relative to the second longitudinal axis, wherein the third tracking coil generates a third output signal indicative of the position of the working member relative to a third tracking coil plane; and
wherein
the first tracking coil, the second tracking coil, and the third tracking coil are radially disposed at 120° positions relative to each other about the second longitudinal axis,
a plane orthogonal to the second longitudinal axis intersects the first tracking coil, the second tracking coil and the third tracking coil,
a radius of the first tracking coil extends in a direction parallel to the first tracking coil plane,
a radius of the second tracking coil extends in a direction parallel to the second tracking coil plane,
a radius of the third tracking coil extends in a direction parallel to the third tracking coil plane, and
the first tracking coil plane, the second tracking coil plane and the third tracking coil plane intersect each other at the second longitudinal axis.

17. The instrument tracking device of claim 16, wherein the body includes:
a first lobe that projects radially from the body and holds the first tracking coil;
a second lobe that projects radially from the body and holds the second tracking coil; and
a third lobe that projects radially from the body and holds the third tracking coil.

18. The instrument tracking device of claim 16, further comprising a longitudinal support member connected to the body and configured to hold a cable, wherein:
- terminal ends of each of the first tracking coil, the second tracking coil and the third tracking coil are electrically connected to wires of the cable; and
- the longitudinal support member prevents separation of the cable from the body.

19. An instrument comprising:
- an elongated housing extending along a first longitudinal axis;
- a working member at a distal tip of the instrument;
- a body having a base and a cap, wherein the cap covers the base, wherein the body extends along a second longitudinal axis and is attached to the elongated housing;
- a first tracking coil disposed on the body and radially offset relative to the second longitudinal axis, wherein a radius of the first tracking coil extends in a direction parallel to a first tracking coil plane, and wherein the first tracking coil generates a first output signal indicative of a position of the working member relative to the first tracking coil plane;
- a second tracking coil disposed on the body and radially offset relative to the second longitudinal axis, wherein a radius of the second tracking coil extends in a direction parallel to a second tracking coil plane, and wherein the second tracking coil generates a second output signal indicative of the position of the working member relative to the second tracking coil plane; and
- a third tracking coil disposed on the body and radially offset relative to the second longitudinal axis, wherein a radius of the third tracking coil extends in a direction parallel to a third tracking coil plane, wherein the third tracking coil generates a third output signal indicative of the position of the working member relative to the third tracking coil plane, wherein
- the first tracking coil, the second tracking coil, and the third tracking coil are disposed at radially equidistant locations around the body,
- the first tracking coil plane, the second tracking coil plane, and the third tracking coil plane intersect each other, and
- a plane orthogonal to the second longitudinal axis intersects the first tracking coil, the second tracking coil and the third tracking coil.

20. The instrument of claim 19, wherein:
- the body has an opening along the second longitudinal axis;
- the body is configured to be attached to the elongated housing such that at least a portion of the elongated housing extends through the opening; and
- the first longitudinal axis and the second longitudinal axis are collinear.

21. The instrument of claim 19, wherein:
- the body includes a cable support member; and
- the cable support member is configured to hold a cable external to the body and between the first tracking coil and the second tracking coil.

22. The instrument tracking device of claim 21, further comprising a printed circuit board attached to the body, wherein:
- the first tracking coil, the second tracking coil, and the third tracking coil are electrically connected to the printed circuit board; and
- the cable is electrically connected to the printed circuit board.

* * * * *